United States Patent
Schöb

(10) Patent No.: US 6,278,251 B1
(45) Date of Patent: Aug. 21, 2001

(54) PERMANENT MAGNETICALLY EXCITED ELECTRICAL ROTARY DRIVE

(75) Inventor: Reto Schöb, Volketswil (CH)

(73) Assignees: Sulzer Electronics AG, Winterthur (CH); Lust Antriebstechnik GmbH, Lahnau (DE)

( * ) Notice: Subject to any disclaimer, the term of this patent is extended or adjusted under 35 U.S.C. 154(b) by 0 days.

(21) Appl. No.: 09/388,263

(22) Filed: Sep. 1, 1999

(30) Foreign Application Priority Data

Sep. 24, 1998 (EP) .................................................. 98810956
Jun. 22, 1999 (EP) .................................................. 99810553

(51) Int. Cl.$^7$ ....................................................... H02P 6/00
(52) U.S. Cl. ........................... 318/293; 318/434; 318/720
(58) Field of Search .................................... 318/138, 254, 318/432, 433, 434, 439, 700, 720, 721, 722, 724, 280, 287, 291, 293

(56) References Cited

U.S. PATENT DOCUMENTS

| | | | |
|---|---|---|---|
| 4,135,120 | * 1/1979 | Hoshimi et al. | 318/138 |
| 4,355,255 | * 10/1982 | Herr et al. | 318/138 X |
| 4,503,369 | * 3/1985 | Nishijima et al. | 318/254 |
| 4,588,933 | * 5/1986 | Sun | 318/254 |
| 4,642,538 | * 2/1987 | Elliott et al. | 318/139 |
| 4,675,583 | * 6/1987 | Berghammer | 318/254 |
| 4,730,150 | * 3/1988 | Lee et al. | 318/254 |
| 4,882,524 | * 11/1989 | Lee | 318/254 |
| 5,155,402 | 10/1992 | Bichler | 310/90.5 |
| 5,216,339 | * 6/1993 | Skybyk | 318/254 |
| 5,300,841 | 4/1994 | Preston et al. | 310/90.5 |
| 5,363,024 | * 11/1994 | Hiratsuka et al. | 318/254 |
| 5,424,595 | 6/1995 | Preston et al. | 310/90.5 |
| 5,491,622 | 2/1996 | Carosa . | |
| 5,541,487 | * 7/1996 | Yorozu | 318/685 |
| 5,543,673 | 8/1996 | Katsumata et al. | 310/90.5 |
| 5,578,880 | 11/1996 | Lyons . | |
| 5,589,744 | * 12/1996 | Brambilla | 318/254 |
| 5,656,910 | * 8/1997 | Erckert | 318/685 |
| 5,920,166 | * 7/1999 | Schlager et al. | 318/439 |

FOREIGN PATENT DOCUMENTS

| | | |
|---|---|---|
| 2276050A | 9/1994 | (GB) . |
| WO 97/07340 | 2/1997 | (WO) . |
| WO 97/08808 | 3/1997 | (WO) . |
| WO 98/11650 | 3/1998 | (WO) . |

OTHER PUBLICATIONS

Patent Abstracts of Japan; vol. 18, No. 681 (E–1649), Dec. 21, 1994 & JP 06 269144 A (Shinko Electric Co. Ltd), Sep. 22, 1994 Abstract.
Patent Abstracts of Japan; vol. 18, No. 434 (E–1592), Aug. 12, 1994 & JP 06 133493 A (Shinko Electric Co. Ltd), May 13, 1994 Abstract.
Patent Abstracts of Japan; vol. 96, No. 7 Jul. 31, 1996 & JP 08 084491 A (Ebara Corp), Mar. 26, 1996 Abstract.
Patent Abstracts of Japan; vol. 17, No. 3 (E–1301), Jan. 6, 1993 & JP 04 236188 A (Toshiba Corp), Aug. 25, 1992 abstract.

* cited by examiner

*Primary Examiner*—Bentsu Ro
(74) *Attorney, Agent, or Firm*—Townsend and Townsend and Crew LLP

(57) ABSTRACT

A permanent magnetically excited electrical rotary drive for a blood pump is proposed, comprising a permanent magnetic rotor and a stator, said stator comprising a drive winding having at least two loops for the production of a magnetic drive field which produces a torque on the rotor, with each loop belonging to a different electrical phase, furthermore comprising a setting device which supplies each loop in each case with a phase current or in each case with a phase voltage as a setting parameter, with the setting device comprising a separate power amplifier for each loop so that the setting parameter for each loop can be regulated independently of the setting parameter for the other loops.

10 Claims, 3 Drawing Sheets

PERMANENT MAGNETICALLY EXCITED ELECTRICAL ROTARY DRIVE

BACKGROUND OF THE INVENTION

1. Field of the Invention

The invention relates to a permanent magnetically excited electrical rotary drive for a blood pump and to a blood pump with a rotary drive of this kind.

2. Description of the Prior Art

Blood pumps, which are usually designed as axial or as centrifugal pumps, serve for the forwarding of blood and are used, for example, in the framework of operations on the heart for maintaining the blood circulation. Furthermore, implantable blood pumps are known which are implanted into the body of the patient for the temporary or chronic support of the heart activity.

In blood pumps it must be ensured that no contamination of the forwarded blood arises. Therefore, the rotor of the electromagnetic drive and/or the pump rotor is preferably magnetically journalled in blood pumps. This magnetic journalling of the rotor can be realized either through separate magnetic bearings, that is ones which are different from the drive; or the magnetic journalling is realized through the stator of the drive.

A rotation pump which is suitable as a blood pump and which is designed as a so-called bearingless motor, which means as an electromagnetic rotary drive with a magnetically contactlessly journalled rotor, with no separate magnetic bearings being present for the rotor, is disclosed in WO-A-96/31934. For this, the stator is designed as a bearing and drive stator which comprises a drive winding and a control winding. With these two windings, a magnetic rotary field can be produced which, on the one hand, exerts a torque on the rotor and which, on the other hand, exerts a transverse force on the rotor which can be set as desired so that its radial position can be actively controlled.

Furthermore, blood pumps, in particular in the case of an implantation into the body, should be compact and space saving, but nevertheless achieve a pump performance which corresponds at least to that of the heart. For this it is e.g. proposed in WO-A-96/31934 to provide the rotor of the bearingless motor with vanes so that the rotor of the rotary drive is identical with the pump rotor, that is, forms an integral rotor. This rotor thus serves as a drive rotor, a bearing rotor and a pump rotor, through which a very compact and high performance blood pump can be realized.

Blood pumps are also known in which the pump rotor by means of which the blood is forwarded is different from the rotor of the rotary drive. The pump rotor is designed as a vaned wheel or rotor, which is set into rotation by the rotor of the rotary drive. For this, blood pumps of this kind can be designed, for example, in accordance with the principle of the gap tube motor or of the gap tube pump respectively; or the pump rotor can be magnetically coupled to the rotor of the rotary drive.

An essential importance, in particular in regard to implantable blood pumps, is assumed by the operating reliability. A problem in known rotary drives for blood pumps is that when faults arise, such as, for example, the failure of an amplifier circuit or the breakage of an electrical line in one of the phases of the drive winding of the stator, a correct functioning of the drive is no longer ensured. A failure of the drive of a blood pump resulting therefrom can, however, have very severe, possibly even fatal results. The invention is thus dedicated to the task of significantly reducing this safety risk.

SUMMARY OF THE INVENTION

The object of the invention is therefore to provide an electrical rotary drive for a blood pump which still enables a correct operation, which means, in particular, a reliable driving of the rotor, even when faults arise.

Thus, in accordance with the invention a permanent magnetically excited electrical rotary drive for a blood pump is proposed, comprising a permanent magnetic rotor and a stator, said stator comprising a drive winding having at least two loops for the production of a magnetic drive field which produces a torque on the rotor, with each loop belonging to a different electrical phase, furthermore comprising a setting device which supplies each loop in each case with a phase current or in each case with a phase voltage as a setting parameter, with the setting device comprising a separate power amplifier for each loop so that the setting parameter for each loop can be regulated independently of the setting parameter for the other loops.

Since the setting parameter, which means the phase voltages or the phase currents, is regulatable for each loop of the drive winding independently of the setting parameters for the other loops and since, in addition, a separate power amplifier is provided for each loop, each electrical phase, by which is meant in each case a loop of the drive winding and the part of the setting device supplying it, can be operated independently of the other electrical phases. Thus, the rotary drive can continue to be operated with a reduced number of phases in the event of a fault in a phase, e.g. the failure of the entire phase, without it being necessary to make concessions to the correct functioning of the rotary drive. Since the rotary drive in accordance with the invention can be operated with a reduced number of phases, it is in principle irrelevant where a fault arises in a phase. Thus, for example, a power amplifier can fail or a breakage in a line in a loop of the drive winding or in the connection between the power amplifier and a loop of the drive winding can occur, or a short circuit in a power amplifier or a winding loop of the drive winding can arise; and in spite of a fault of this kind a continued operation of the rotary drive is possible. As a result of this high fault tolerance, the rotary drive in accordance with the invention brings about a considerable increase in the operating reliability.

Depending on how many phases the rotary drive in accordance with the invention is designed with, it can even continue to be operated in the event of the failure of a plurality of phases. The minimum requirement for the capability of functioning of the rotary drive is that one phase, that is, a loop of the drive winding and the power amplifier supplying it, still operates without fault.

The rotary drive in accordance with the invention, with its design which is at least two-phased in its fault-free normal condition, is a permanent magnetically excited rotary field motor, thus, in particular, a permanent magnetically excited synchronous or a brushless d.c. motor (in spite of its generally usual name, the latter is in essence a rotary field motor). This means that the drive field which is produced by the stator is a magnetic rotary field which drives the permanent magnetic rotor. If only one fault-free phase still remains for operation through a fault in one or more phases, then the rotary field motor becomes a single phase a.c. motor.

Since an arbitrarily large supply of energy is in general not available for blood pumps, and in particular for implanted blood pumps, it is important for the rotary drive of a blood pump to operate as economically as possible and with as low an energy consumption as possible. Since the rotary drive in accordance with the invention is permanent magnetically excited, and thus has a permanent magnetically excited rotor, it is particularly suitable for blood pumps in contrast to field excited rotary drives, since no current and thus no energy is required for the field excitation in a permanent magnetically excited rotary drive.

In accordance with a first exemplary embodiment of the rotary drive in accordance with the invention a loadable star point is provided, which is connected to each loop of the drive winding. In usual multiple phase, e.g. three phase drive windings the three loops are in each case connected to a common star point, with it being necessary for the condition to be fulfilled that the sum of the phase currents is always zero at the star point. Through the measure of making the star point loadable, which means placing it at a loadable potential, this requirement can be omitted so that each phase current or each phase voltage respectively can be regulated independently of the others.

Two stabilized voltage sources are preferably provided in this exemplary embodiment for supplying the setting device, with the voltage sources having a common pole and with the loadable star point lying at the same potential as the common pole of the voltage sources. The common pole can, for example, lie at ground potential. The one voltage source then delivers a positive supply voltage and the other voltage source a negative supply voltage.

In a second preferred exemplary embodiment of the rotary drive in accordance with the invention, each loop of the drive winding has two electrical connection lines, with the connection lines of one loop in each case being separate from and independent of the other connection lines. Each power amplifier is then connected to exactly two connection lines, with these two connection lines belonging to the same loop. In this exemplary embodiment, thus, for each loop of the drive winding two connection lines are led up to the power amplifier which supplies this loop. There is thus no common point of connection, such as e.g. a star point, at which connection lines which belong to different loops can be led together or electrically conductingly connected respectively. Through this measure as well it is also possible to regulate the setting parameter (phase current or phase voltage) for each loop independently of the setting parameter for the other loops.

For practical reasons it is preferred in this that each power amplifier is designed as a H bridge circuit.

A further advantageous measure consists in providing a monitoring module which deactivates one of the electrical phases when a fault arises in it. A needless energy consumption in a faulty phase, which can, for example, be caused by a short circuit, can thereby be avoided.

It is, in particular, advantageous to provide an excessive current safety device for each electrical phase in order that the associated phase is switched off when a short circuit arises. A large asymmetrical loading of the energy source which feeds the power amplifier can thereby be avoided.

The rotary drive in accordance with the invention can, in particular, also be designed as a bearingless motor (in the already explained sense) which journals the rotor of the rotary drive magnetically, with the stator being designed as a drive and bearing stator, which further comprises a control winding in addition to the drive winding.

Furthermore, through the invention a blood pump with a permanent magnetically excited electrical rotary drive in accordance with the invention is proposed. Through the fault tolerance of the rotary drive a blood pump of this kind is distinguished by a very high operating reliability so that it can also be used, in particular, for implantation into a body. In particular, in combination with a fault-tolerant magnetic bearing apparatus for the rotor, a blood pump can be realized which has only a minimal safety risk, if any.

In order to be able to design the blood pump particularly compactly, the rotor of the rotary drive can be designed as a pump rotor for forwarding the blood, which means that the rotor of the rotary drive is identical to the pump rotor in a manner analogous to that which is disclosed in the already cited WO-A-96/31934 for the integral rotor.

DETAILED DESCRIPTION OF THE PREFERRED EXEMPLARY EMBODIMENTS

Figure 1:
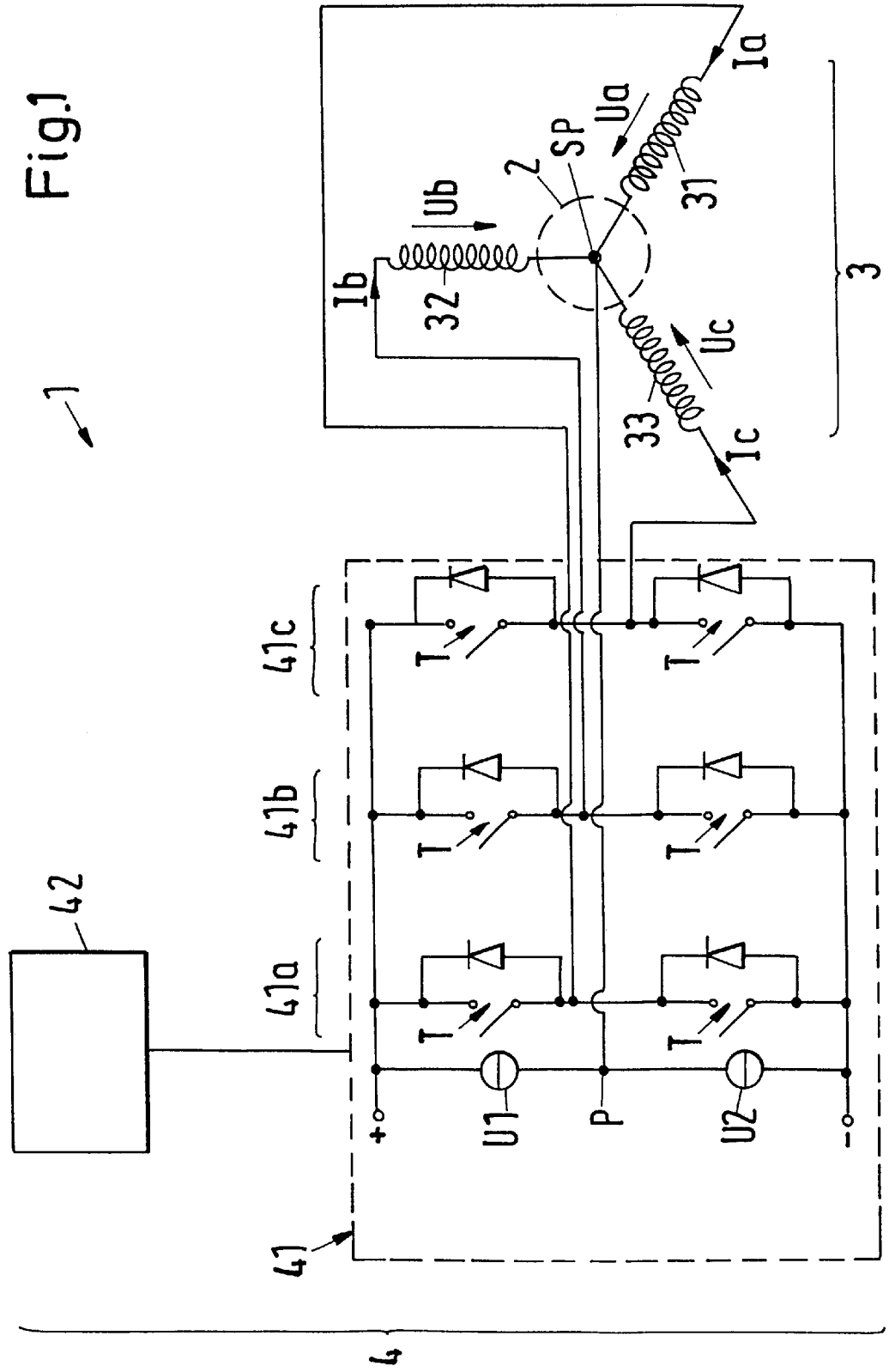
FIG. 1 is a schematic illustration of a first exemplary embodiment of the rotary drive in accordance with the invention.

FIG. 1 shows, in a schematic illustration, a first exemplary embodiment of the permanent magnetically excited electrical rotary drive in accordance with the invention, which is designated in its entirety by the reference symbol 1. The rotary drive 1 comprises a permanent magnetic rotor 2, a stator 3 and a setting device 4 with an amplifier element 41 and a regulation unit 42.

The stator 3 has a drive winding which has three loops 31, 32, 33 in this exemplary embodiment, each of which belongs to a different electrical phase, which means that the drive winding is designed to be three phased. By means of the drive winding a magnetic rotary field can be produced as a drive field which produces a torque on the rotor 2, through which the latter is set into rotation.

In the following, reference is made to the case, which is particularly important in practice, that the drive winding is designed to be three phased with three loops 31, 32, 33. It is, however, clear that the rotary drive in accordance with the invention can analogously also be designed with two phases, which means with a drive winding having two loops, or with n phases (with n>3), which means with a drive winding comprising n loops.

The drive winding with the three loops 31, 32, 33 is wound on the stator 3 in a manner which is known per se and thereby forms a plurality of discrete coils for producing the magnetic drive field. In this way a plurality of discrete coils can be connected to one another electrically in a parallel circuit or in a series circuit. The totality of all of the discrete coils which are electrically connected to one another in parallel or in series will be designated as a loop 31 or 32 or 33 of the drive winding. Naturally, it is also possible that each loop 31, 32, 33 comprises only one discrete coil.

Each loop together with the part of the setting device 4 supplying it forms a separate electrical phase. The setting device 4 can supply each loop 31, 32, 33 in each case with a phase current Ia, Ib, Ic or a phase voltage Ua, Ub, Uc as setting parameter. The setting device 4 can thus be designed as a current controller or as a voltage controller for the drive winding.

The first exemplary embodiment is thus a three phase, permanent magnetically excited rotary field motor. In accordance with the invention, the setting device 4 comprises a separate power amplifier 41a, 41b, 41c for each loop 31, 32, 33 so that the setting parameter Ia, Ib, Ic or Ua, Ub, Uc respectively for each loop 31, 32 or 33 is regulatable independently of the setting parameter for the other loops.

In the first exemplary embodiment, the three power amplifiers 41a, 41b, 41c are, in each case, bridge branches of an amplifier element 41, which are, for example, parts of a three phase rotary current controller, of which only the power part is illustrated in FIG. 1. The signal processing and regulation device, which can, for example, be completely or partly integrated into the amplifier element 41, which is designed as an integrated circuit, are collected together in a symbolic manner in the regulation unit 42 in FIG. 1.

A bridge branch of the amplifier element 41 is in each case provided as a separate bipolar power amplifier 41a, 41b, 41c for each loop 31, 32, 33 of the drive winding. Each bridge branch can supply the associated loop 31 or 32 or 33 with the respective phase current Ia, Ib, Ic or the respective phase voltage Ua, Ub, Uc by means of switching transistors T and recovery diodes in a manner which is known per se. The switching transistors T are preferably field effect transistors (FETs). The amplifier element 41 is operated with two operating potentials, which are designated by + and − in FIG. 1. These operating potentials +,− are d. c. potentials. Two stabilized voltage sources U1 and U2 which have a common pole P are provided for the supply of the amplifier element 41. The common pole P lies at a potential which is between the two operating potentials + and −, for example, at ground potential. The one voltage source U1 then delivers the positive supply voltage relative to the common pole P and the other voltage source U2 the negative supply voltage relative to the common pole P.

Each loop 31, 32, 33 is connected, on the other hand, to the bipolar power amplifier 41a, 41b, 41c which supplies it. On the other hand, each loop is connected to a common loadable star point SP which lies at the same potential as the common pole P of the voltage sources U1, U2. The star point SP is, for example, connected directly to the common pole P of the voltage sources U1, U2 via an electrical conductor. The three loops 31, 32, 33 of the drive winding are thus connected in a star point circuit, with the star point SP, however, being loadable, which means that it is connected to a loadable potential so that, apart from the three phase currents Ia, Ib, Ic, an additional current can flow off via the star point SP or flow into the latter, respectively. This means that the usual star point condition that the sum of the phase currents Ia, Ib, Ic must always be zero at the star point SP is no longer required in this circuit. This has, as a result, that each phase current Ia, Ib, Ic can be regulated completely independently of the other phase currents. Current measurement devices (not illustrated) can be provided in the individual phases in each case for the determination of the individual phase currents Ia, Ib, Ic.

In the normal operating state, which means when all three phases are fault free, the three phase rotary drive 1 operates in the manner which is known per se. The speed of rotation of the rotor 2 is regulated by means of a speed of rotation regulator, which is, for example, integrated into the regulation unit 42. Furthermore, sensors (not illustrated) can be provided, from the signal of which the speed of rotation regulator determines the momentary speed of rotation of the rotor 2. If the speed of rotation deviates from a predeterminable desired speed of rotation, then the speed of rotation regulator modifies the individual phase currents Ia, Ib, Ic or the individual phase voltages Ua, Ub, Uc respectively through a corresponding excitation of the amplifier unit in such a manner that the rotor 2 achieves its desired speed of rotation.

If a fault arises in one of the electrical phases, for example, an interruption in an electrical conductor of a loop 31, 32, 33, then, in principle, no measure is required. As soon, as the speed of rotation regulator detects a deviation of the momentary rotor speed of rotation from the desired speed of rotation, which, for example, results from the failure of one of the loops 31, 32 or 33, then the speed of rotation regulator automatically increases the phase currents or the phase voltages, respectively, in the two fault free loops so that the rotor again runs with its desired speed of rotation. This is possible because the individual phase currents Ia, Ib, Ic or the individual phase voltages Ua, Ub, Uc, respectively, can be regulated completely independently of one another. A correct functioning of the rotary drive 1 is thereby also possible with the phases which still remain fault free even in the event of a complete failure of a phase, which is, for example, caused by the failure of a bipolar power amplifier 41a, 41b, 41c or by a line defect in one of the loops 31, 32, 33 or in the connection between a loop and the associated power amplifier.

In a three or more phase embodiment of the rotary drive 1, the latter can still be correctly operated with the remaining fault free phase or phases even in the event of the failure of two or more phases. The minimum requirement is that one of the phases still operates faultlessly. If only one of the phases is still fault free, then the rotary drive 1 operates as a single phase a. c. motor. In this case, as long as the rotary drive 1 is not stopped, it continues to rotate, and thus still operates correctly. If, however, an a. c. motor of this kind is stopped, it is possible, depending on the relative position of rotor 2 and stator 3, that the rotary drive 1 can no longer be started up. This can be remedied wherein the stator 3 is designed in such a manner that the rotor 2 comes to a stop in a predetermined "rest position" when it is stopped which is chosen in such a manner that the rotor 2 can start up again from this rest position. This measure is sufficiently known from single phase a. c. motors and will, therefore, not be explained in more detail here.

Figure 2:
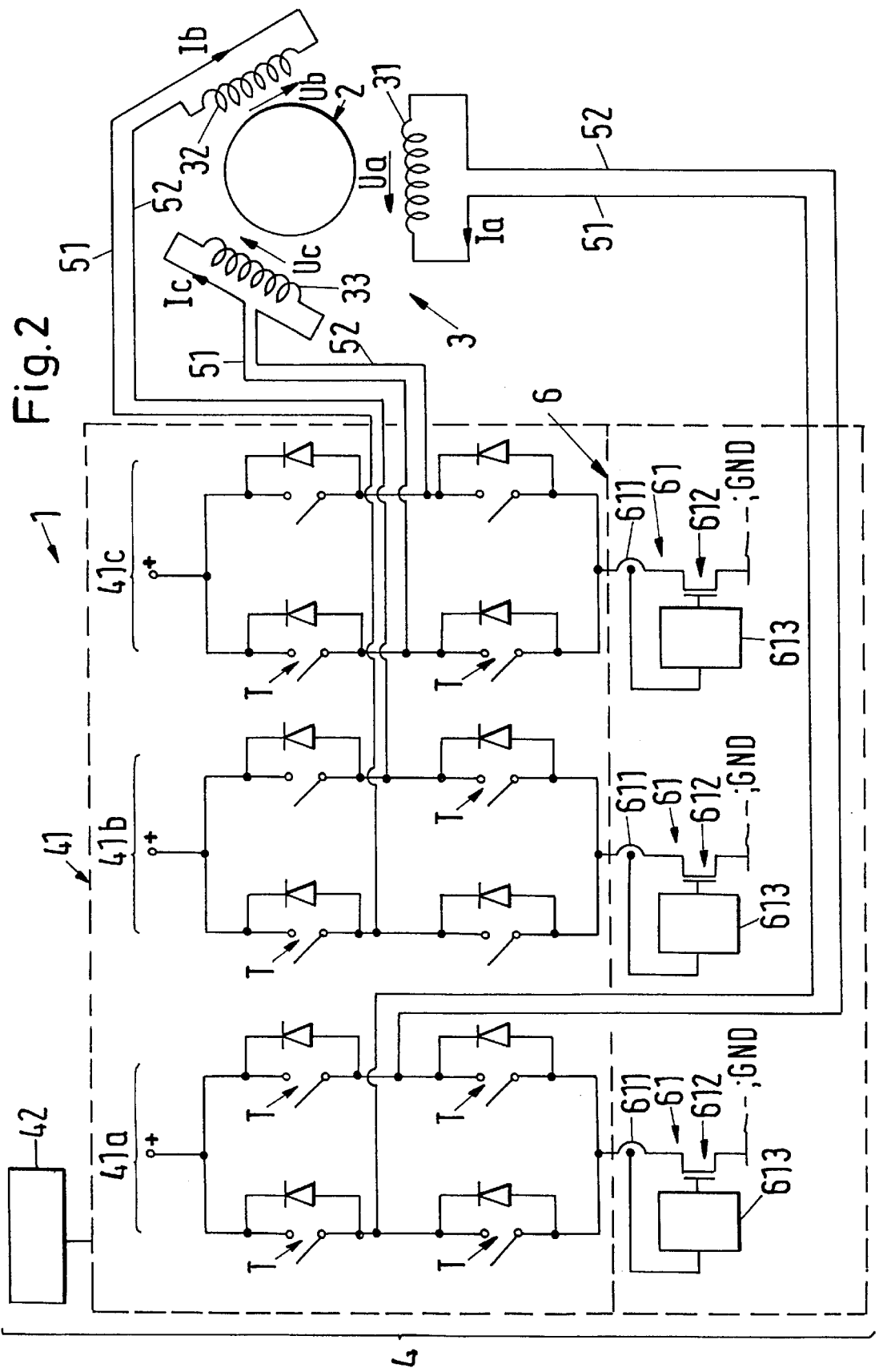
FIG. 2 is a schematic illustration of a second exemplary embodiment of the rotary drive in accordance with the invention.

FIG. 2 shows in a schematic illustration a second exemplary embodiment of the rotary drive 1 in accordance with the invention, with parts which are identical or equivalent in function being provided with the same reference symbols as in FIG. 1. In the following, the differences from the first exemplary embodiment will be described; otherwise the explanations with respect to the first exemplary embodiment also hold for the second exemplary embodiment in an analogous manner.

In the second exemplary embodiment, each loop 31, 32, 33 of the drive winding of the stator 3 has, in each case, two electrical connection lines 51 and 52, with the connection lines 51, 52 of one loop in each case being separate and independent of the connection lines 51, 52 of the other loops. Thus, in contrast to the first exemplary embodiment, no common star point is provided to which each loop 31, 32, 33 of the drive winding is connected, but rather, for each loop both connection lines 51, 52 are, in each case, led out of the stator 3 and separately connected to the power amplifiers 41a, 41b, 41c of the amplifier element 41. Thus, each power amplifier 41a, 41b, 41c is connected to exactly two connection lines 51, 52 which belong to the same loop 31 or 32 or 33.

As FIG. 2 shows, the individual bipolar power amplifiers 41a, 41b, 41c for the loops 31, 32, 33 are, in each case, designed as an H bridge circuit, with a separate power amplifier being provided for each phase or for each loop 31, 32, 33 of the drive winding, respectively, so that an independent regulation of the individual phase currents Ia, Ib, Ic or of the individual phase voltages Ua, Ub, Uc, respectively, is possible. The H bridge circuits are realized with switching transistors T and recovery diodes in a manner which is known, per se, and are operated with the operating potentials + and −. The operating potential − is, for example, the ground potential GND. The switching transistors T are preferably field effect transistors (FETs) and, in particular, power MOS-FETs.

The theoretical mode of operation of the second exemplary embodiment is the same as that of the first exemplary embodiment.

In the second exemplary embodiment as well no special measures need, in principle, be taken in order to continue operating the rotary drive 1 in the event of a failure of one or more phases with the remaining faultless phases or with the remaining faultless phase, respectively. In particular, the rotary drive can still continue to be operated even if a short circuit arises in one phase, e.g. in a loop 31, 32, 33 or in a switching transistor T of the associated power amplifier 41a, 41b, 41c. Since, however, the flowing of short circuit currents also means an unnecessary and useless energy consumption, a monitoring module 6 is preferably provided which deactivates one of the electrical phases when a fault, in particular, a short circuit, arises in this phase. The monitoring module 6 comprises an excessive current safety device 61 for each phase. As FIG. 2 shows, an excessive current safety device 61 is in each case inserted between the H bridge circuit and one of the operating potentials +,−. The excessive current safety device 61 is preferably provided in series between the H bridge circuit and the operating potential−, which is the ground potential GND here.

The excessive current safety device 61 comprises a current measurement device 611, a switching element 612, which is preferably a FET, as well as an excessive current switchoff device 613. The excessive current switchoff device 613 monitors the intensity of the flowing current by means of the current measurement device 611. If the latter exceeds a predeterminable threshold value, the excessive current switchoff device 613 opens the switching element 612, through which the associated phase is switched off.

The excessive current safety device 61 can, in each case, alternatively also be a rapid circuit breaker, for example a fuse, which is arranged in series between the H bridge and one of the operating potentials +,−.

An excessive current safety device can, of course, also be built in an analogous manner into the bridge branches of the exemplary embodiment illustrated in FIG. 1.

Alternatively or as supplement, the monitoring module 6 can also comprise other elements in order to switch off one phase in the event of a fault in this phase. For example, means can be provided in the monitoring module 6 in order to actuate the switching transistors T of the associated power amplifier 41a or 41b or 41c in such a manner that when a fault arises in a phase, no current flows any longer in this phase (opening of the switches). The monitoring module 6 can furthermore have means for detecting faults.

In deviation from the two exemplary embodiments described, other embodiments of the amplifier element 41 are naturally also possible, for example, other forms of switching amplifiers or analog amplifiers. What is important, however, is that the amplifier element 41 is designed in such a manner that it can be operated bipolarly, by which is meant that both the phase currents and the phase voltages can take on a positive and negative sign. In addition, the amplifier element 41 must be able to supply each phase with a setting parameter (phase current Ia, Ib, Ic or phase voltage Ua, Ub, Uc respectively) in each case which can be regulated independent of the setting parameters for the other phases.

Figure 3:
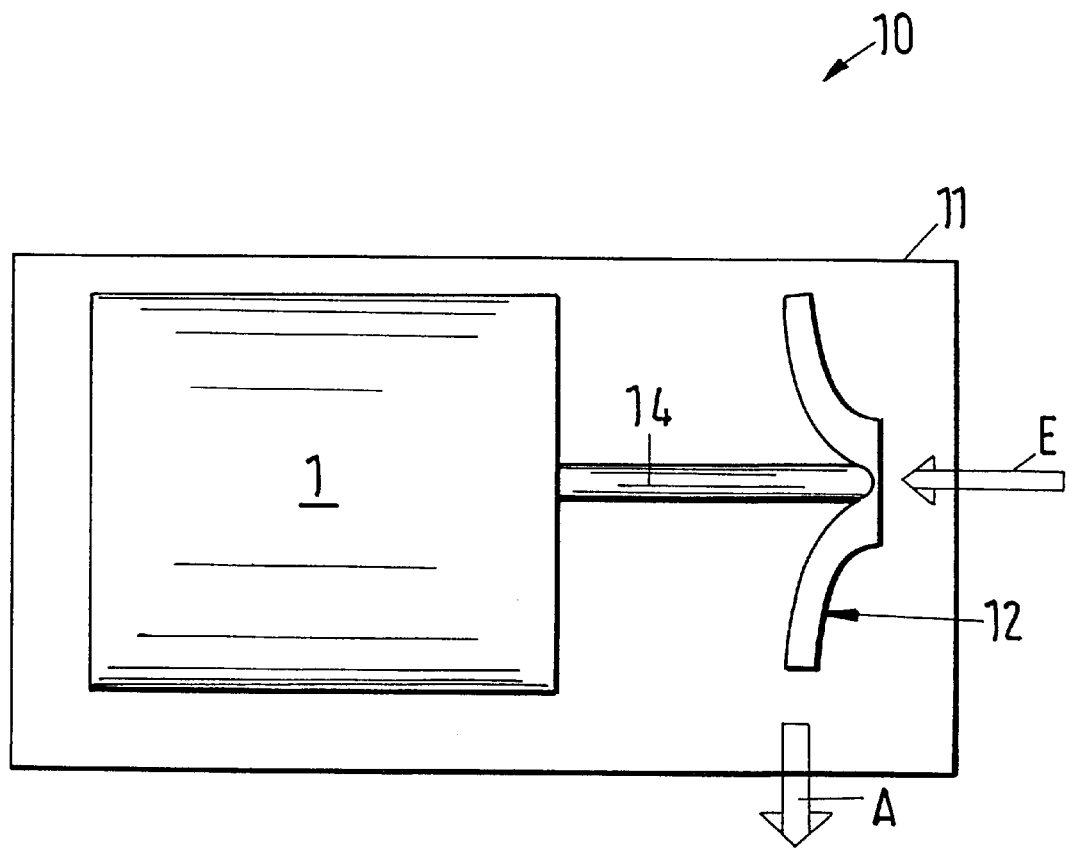
FIG. 3 is a schematic illustration of a blood pump with a rotary drive in accordance with the invention.

FIG. 3 shows, in a highly schematic manner a blood pump 10 which is operated with a rotary drive 1 in accordance with the invention. The blood pump 10 comprises a housing 11 in which a pump rotor 12 which is formed as a rotor with a plurality of vanes or blades is provided. The pump rotor 12 is arranged on an axis 14 and rotationally fixedly connected to the latter. The axis 14 is driven by the rotor 2 of the rotary drive 1. The blood pump 10 is formed here as a centrifugal pump. Through an input which is connected to the blood circulatory system the blood to be forwarded arrives at the pump rotor 12 as is indicated by the arrow E in FIG. 3 and is forwarded to the output by the rotating pump rotor 12. Through the output, the blood arrives back into the blood circulatory system, as is indicated by arrow A in FIG. 3.

The blood pump 10 with the rotary drive 1 can, for example, be designed in accordance with the principle of the gap tube pump or of the gap tube motor, respectively.

The axis 14 and/or the rotor 2 of the rotary drive 1 can be journalled by means of at least one magnetic bearing apparatus. For this, a separate magnetic bearing apparatus, that is, one which is different from the rotary drive 1, can be provided for the rotor 2 or the axis 14, respectively. It is, however, also possible that the magnetic bearing apparatus is integrated into the rotary drive 1. For this, the rotary drive 1 can be designed as a bearingless motor, as is, for example, disclosed in WO-A-96/31934. The bearingless motor owes its name to the fact that the stator 3 is designed as a drive and bearing stator, which magnetically both journals and drives the rotor 2. This means that in a bearingless motor the magnetic bearing and the rotary drive form an inseparable physical unit. In the bearingless motor the stator 3 further comprises, in addition to the drive winding, a control winding. With these two windings a magnetic rotary field can be generated which, on the one hand exerts a driving torque on the rotor 2, and which on the other hand exerts a transverse force on the rotor 2 which can be set as desired so that its radial position can be actively regulated. With respect to the axial direction and with respect to physical tiltings relative to the axis of rotation, the permanent magnetically excited rotor 2 is passively magnetically, that is not actively excitably, stabilized by reluctance forces. With respect to further details, reference is made here to WO-A-96/31934. Additional bearings, such as, for example, magnetic axial bearings or hydrodynamic bearings, can, however, also be provided for the journalling of the rotor 2 of the rotary drive 1 or of the axis 14, respectively.

A further variant of the blood pump 10 consists in designing the rotor 2 of the rotary drive 1 as a pump rotor for forwarding the blood. In this embodiment, which is designated in WO-A-96/31934 as an integral rotor, the pump rotor 12 is identical to the rotor 2 of the rotary drive 1. With respect to concrete examples of how a rotor 2, 12 of this kind can be designed, reference is made to WO-A-96/31934. Since the rotor 2 of the rotary drive is designed as a pump rotor with vanes or blades for forwarding the blood, a particularly space saving and compact blood pump can be realized.

For a particularly reliable blood pump 10, it is advantageous if, in addition to the fault-tolerant rotary drive 1, a likewise fault-tolerant magnetic bearing apparatus is provided for the rotor 2 or the axis 14, respectively. This holds both for the case that the magnetic bearing apparatus is integrated into the rotary drive 1 in accordance with the principle of the bearingless motor, and for the case that at least one separate magnetic bearing apparatus is provided for the rotor 2 or the axis 14 respectively, that is, one which is different from the rotary drive 1.

A fault-tolerant magnetic bearing apparatus of this kind is disclosed in European patent application No. 98810956.7. This fault-tolerant magnetic bearing apparatus comprises a stator (the bearing stator) with a control winding having at least three loops for producing a magnetic control field, by means of which the position of the rotor 2 or of the axis 14, respectively, with respect to the bearing stator can be regulated, with each loop belonging to a different electrical phase, and a setting device which supplies each loop with in each case a phase current or in each case a phase voltage in a first operating mode. Means are provided in order to regulate the setting parameter for each loop independently of the setting parameter for the other loops. Furthermore, a monitoring unit is provided which can switch over the bearing apparatus into a second operating mode in which a reduced number of phases, which is at least two, generates the magnetic field.

The magnetic control field is a magnetic rotary field.

The magnetic bearing apparatus in accordance with European patent application No. 98810956.7 can be designed either in accordance with the principle of the bearingless motor or as a separate magnetic bearing apparatus. In the first named case the bearing stator is identical to the stator 3 of the rotary drive 1, which is consequently designed as a drive and bearing stator. This means that in addition to the at least two-phased drive winding the at least three-phased control winding is furthermore provided on the same stator.

The fault-tolerant bearing apparatus can be operated in two operating modes. In the first operating mode, the magnetic control field is generated by all phases of the three or more phase control winding, thus by all its loops. In the second operating mode, the magnetic control field is now produced with only a reduced number of phases, which, however, amounts to at least two. Thus, all loops of the control winding are no longer used; one or more loops of the control winding are "switched off" in this second operating mode. A two phase control winding is sufficient in order to generate the control field which is required for the regulation of the radial position of the rotor 2 or of the axis 14, respectively, with respect to the bearing stator. For this, it is, however, necessary that the two phase currents or phase voltages can be regulated independently of one another.

Through the two operating modes it is possible in the event of the occurrence of a fault in one of the phases, for example, in the event of the failure of a winding loop as a result of a line breakage or of a short circuit or in the event of a failure of the amplifier which supplies this phase, to continue to operate the bearing apparatus with a reduced number of phases without concessions in the correct functioning of the magnetic bearing being required. This fault tolerance, namely of still ensuring a reliable operation of the magnetic bearing apparatus even in the event of a failure of a phase of the control winding, means an enormous increase in the operating reliability in comparison with other magnetic bearings.

The monitoring unit preferably monitors the functioning of each individual phase and on the occurrence of a fault in a phase switches the bearing apparatus into the second operating mode in which only those phases which are without a fault produce the magnetic control field any longer.

As has already been mentioned, for the case that the control winding is operated in only two phases any longer, it is necessary for the phase current or the phase voltage in the two loops of the control winding to be regulatable independently of one another. Usually the phase currents or the phase voltages are provided by an amplifier unit which is contained in the setting device.

In a first embodiment of the fault-tolerant bearing apparatus, the means for the independent regulation of the setting parameter (phase current or the phase voltage) comprise a loadable star point to which each phase is connected and which is placed at a potential which lies between the two operating potentials of the amplifier unit. In usual three phase control windings the three loops are, in each case, connected to a common star point, with it being necessary that the condition is fulfilled that the sum of the phase currents is zero at the star point. Through the measure of making the star point loadable, which means placing it at a loadable potential, this condition can be eliminated so that each phase current or each phase voltage respectively can be regulated independently of the others.

In a second embodiment, the amplifier unit comprises as a means for the independent regulation of the setting parameter (phase current or each phase voltage) a separate power amplifier for each phase which is designed as an H bridge circuit. This measure as well enables an independent regulation of the individual phase currents or the phase voltages for the bearing apparatus.

In accordance with a further aspect the fault-tolerant magnetic bearing apparatus has at least three position sensors for determining the radial position of the rotor 2 and 4 of the axis 14, respectively, in a stator system, which is stationary with respect to the bearing stator. Since theoretically two position sensors are sufficient in order to determine the radial position of the rotor and of the axis in the stator system, a fault tolerance of the position sensor mechanism, which is essential for the regulation of the position of the object to be journalled and thus for the operation of the bearing apparatus, can be achieved through the use of at least three position sensors.

In the event of the failure of a position sensor, the radial position of the object is still not uniquely possible by means of the remaining position sensors. This means a further increase of the operating reliability of the magnetic bearing apparatus.

A position unit is preferably provided which converts the signals of the position sensors by means of a transformation into a two component position signal, the one component of which represents the X coordinate and the other component of which represents the Y coordinate of the object to be journalled in the stator system.

In a preferred the three position sensors are arranged in such a manner that, in each case, two adjacent position sensors are displaced relative to one another by an angle of 120° with respect to the peripheral direction of the bearing stator. In this arrangement it is possible in a particularly simple way, to compensate for the failure of a position sensor. If the defective position sensor delivers the signal zero, no measure at all is necessary for the compensation, in principle. The transformation into the two component position signal can be carried out with an unchanged transformation matrix and nevertheless leads to a correct position regulation.

The position unit preferably monitors the functioning of the position sensors. This can, for example, take place in such a manner that the position unit tests for each position sensor whether the signal delivered by it or the average value of a plurality of its signals lies within a predeterminable tolerance range. It is also possible that the position unit monitors the other position sensors by means of the signal of at least one of the position sensors.

If the position unit detects the occurrence of a fault in the above mentioned 120° arrangement of the position sensors, then it sets the signal of the associated position sensors to zero prior to the transformation and then carries out the transformation with the same transformation matrix as in the case that all position sensors are operating correctly.

If the angle between adjacent position sensors does not amount to 120°, then, in general, a change of the transformation is necessary in the event of a failure of a position sensor in order to ensure a correct position regulation.

In the event of the occurrence of a fault in a position sensor the position unit can then select another transformation for the determination of the position signal in which only the signals of fault free position sensors enter.

With respect to further details of a fault-tolerant magnetic bearing apparatus of this kind, reference is made to European patent application No. 98810956.7.

If the permanent, magnetically excited rotary drive 1 and the fault-tolerant magnetic bearing are formed together as a bearingless motor, the rotor 2 is preferably designed in disc or ring shape.

What is claimed is:

1. A permanent magnetically excited electrical rotary drive, comprising a permanent magnetic rotor and a stator, said stator comprising a drive winding having at least two loops for the production of a magnetic drive field which produces a torque on the rotor, with each loop belonging to a different electrical phase, comprising a setting device which supplies each loop in each case with a phase current or in each case with a phase voltage as a setting parameter, wherein each phase includes a separate switching means for switching off only its associated phase in a case of an excessive current in the associated phase, and wherein the setting device comprises a separate bipolar power amplifier for each loop so that the setting parameter for each loop can be regulated by a closed loop control independently of the setting parameter for the other loops.

2. A rotary drive in accordance with claim 1, in which each loop of the drive winding has two connection lines, with the connection lines of a loop in each case being separate and independent of the other connection lines, and in which each power amplifier is connected to exactly two connection lines, with these two connection lines belonging to the same loop.

3. A rotary drive in accordance with claim 1, in which each power amplifier is designed as an H bridge circuit.

4. A rotary drive in accordance with claim 1, comprising a monitoring module which deactivates one of the electrical phases when a fault arises therein.

5. A rotary drive in accordance with claim 1, in which an excessive current safety device is provided for each electrical phase.

6. A rotary drive in accordance with claim 1, in which the rotary drive is designed as a bearingless motor which magnetically journals the rotor of the rotary drive, with the stator being designed as a drive and bearing stator which furthermore comprises a control winding in addition to the drive winding.

7. A blood pump comprising a permanent magnetically excited electrical rotary drive in accordance with claim 1.

8. A blood pump in accordance with claim 7, with the rotor of the rotary drive being designed as a pump rotor for the forwarding of the blood.

9. A blood pump in accordance with claim 7, comprising a fault-tolerant magnetic bearing apparatus for a rotor or for an axis, said bearing apparatus comprising a bearing stator with a control winding having at least three loops for producing a magnetic control field by means of which the position of the rotor or of the axis respectively with respect to the bearing stator can be regulated, with each loop belonging to a different phase, as well as a setting device which in a first operating mode provides each loop with in each case a phase current or with in each case a phase voltage as setting parameter, with means being provided in order to be able to regulate the setting parameter for each loop independently of the setting parameter for the other loops, as well as a monitoring unit which can switch over the bearing apparatus into a second operating mode in which a reduced number of phases, which is at least two, produces the magnetic control field.

10. A permanent magnetically excited electrical rotary drive, comprising a permanent magnetic rotor and a stator, wherein the rotary drive is designed as a bearingless motor which magnetically journals the rotor of the rotary drive, said stator comprising a drive winding having at least two loops for the production of a magnetic drive field which produces a torque on the rotor, and being designed as a drive and bearing stator which furthermore comprises a control winding in addition to the drive winding, with each loop belonging to a different electrical phase, furthermore comprising a setting device which supplies each loop in each case with a phase current or in each case with a phase voltage as a setting parameter, wherein the setting device comprises a separate bipolar power amplifier for each loop so that the setting parameter for each loop can be regulated by a closed loop control independently of the setting parameter for the other loops.

* * * * *